United States Patent

Buettner et al.

[11] Patent Number: 5,723,579
[45] Date of Patent: Mar. 3, 1998

[54] FIBRINOGEN BINDING PEPTIDES

[75] Inventors: Joseph A. Buettner, Raleigh; Christopher A. Dadd, Cary; George A. Baumbach, Knightdale; David J. Hammond, Raleigh, all of N.C.

[73] Assignee: Bayer Corporation, Berkeley, Calif.

[21] Appl. No.: 595,718

[22] Filed: Feb. 2, 1996

[51] Int. Cl.$^6$ .......................... A61K 38/08; C07K 7/04; C07K 14/75

[52] U.S. Cl. .......................... 530/329; 530/330; 530/382; 530/413

[58] Field of Search .......................... 530/330, 329, 530/382

[56] References Cited

FOREIGN PATENT DOCUMENTS 9426930  11/1994  WIPO .

OTHER PUBLICATIONS

Poulsen, K. et al. Competitive inhibitors of renin. Biochemistry, 12(20), 3877–82 1973.

Nayersina, R. et al HLA A2 restricted cytotoxic T lymphocyte responses to multilpe hepatitis B surface antigen epitopes during hepatitis B virus infection. J. Immunol., 150(10), 4659–71 1993.

Baumann, M. et al. Molecular cloning, characterization and functional expression of therat liver interleukin 6 receptor. J. Biol. Chem. 265, 19853–19862 1990.

Laddaga, R. et al. Nucleotide sequence and expression of the mercurial-resistance operon from Stahylococcus aureus plasmid p1258. Proc. Natl. Acad. Sci. USA, 84, 5106–5110 1987.

Sugita, T. Functional murine interleukin 6 receptor with the intracisternal A particle gene product at its cytosolic domain. J. Exp. Med. 171, 2001–2009 1990.

Primary Examiner—Cecilia J. Tsang
Assistant Examiner—Michael Borin
Attorney, Agent, or Firm—James A. Giblin; Michael J. Beck

[57] ABSTRACT

Peptides which bind to fibrinogen are disclosed. These peptides have available fibrinogen binding domains having a Phe-Leu-Leu-Val or Leu-Leu-Val-Pro sequence. The preferred peptide is a 6-mer having the sequence Phe-Leu-Leu-Val-Pro-Leu (SEQ ID NO:1). A method of using these peptides in an affinity chromatography process to purify fibrinogen is described.

10 Claims, 6 Drawing Sheets

FIBRINOGEN BINDING PEPTIDES

BACKGROUND OF THE INVENTION

1. Field

This invention is concerned generally with identifying protein-ligand interactions, and specifically with peptide ligands which bind fibrinogen and which may be used in a method for the affinity purification of fibrinogen.

2. Background

Fibrinogen is a plasma precursor of the major protein of dotted blood, fibrin. Fibrinogen is a glycoprotein comprised of three pairs of polypeptides (A$\alpha$, B$\beta$, and $\gamma$) joined by disulfides. Thrombin cleavage of the A$\alpha$ and B$\beta$ chains converts fibrinogen into fibrin and initiates dotting. Fibrinogen has been used commercially for use in hemostatic preparations, typically called fibrin glues or sealants.

Preparation of fibrinogen concentrates has been performed by precipitation methods from whole plasma, cryoprecipitate, or Cohn fraction I for use in tissue glues. The most crude preparations merely use cryoprecipitated protein directly for use as a fibrin sealant, typically made from autologous plasma (Kingdon et al., 1994). Larger scale procedures depend upon use of ethanol (Blomback and Blomback, 1956), ammonium sulfate (Takeda, 1966) or $\beta$-alanine and/or glycine (Jakobsen and Kierulf, 1973) to effect differential solubility. These concentrates are mixtures of many other plasma proteins, including Factor XIII and fibronectin, and also less desirable plasmin, plasminogen, fibrinogen degradation products (fragments D and E) and fibrin protomers. Inhibition of plasmin by the addition of $\epsilon$-aminocaproic acid is usually required to yield clottable fibrinogen.

Chromatographic isolation methods use gel filtration or ion exchange resins to prepare intermediate purity concentrates (reviewed in Furlan, 1984). Ultrafiltration has also been claimed as a method (Kopf and Morse, 1993). Affinity methods have also been introduced for high purity enrichment of fibrinogen from plasma. Protamine has been used to purify fibrinogen (Dempfle & Heene, 1987a), although fibrinogen degradation products and protofibrils of fibrin also co-purify (Dempfle & Heene, 1987b). Immobilized monomeric fibrin has been shown to bind and purify fibrinogen (Matthias et al, 1975). The antibiotic, Ristocetin, has been immobilized and used to bind fibrinogen (Suzuki et al., 1980). Immunoaffinity chromatography has been developed and is especially useful for analytical applications (Merskey et al., 1980; McConnell & Anderson, 1993).

*Peptide Ligand Chromatography* Kuyas, et al. (1990) purified fibrinogen from plasma on a column of GPRPK-Sepharose. (SEQ ID NO 4) The peptide GPRP is an analogue of the carboxy side (GPRVVERHK (SEQ ID NO 5)) of the fibrinogen A$\alpha$-chain exposed upon cleavage by thrombin. This sequence is the binding region for initial polymerization by a carboxy terminal sequence on the $\gamma$ chain of fibrinogen. (Amino acid abbreviations are as typically used in the art and are described in Scholz et al., 1993.)

SUMMARY OF THE INVENTION

We have now discovered a group of peptides characterized by their ability to bind fibrinogen. These peptides have available fibrinogen binding domains selected from the group consisting of Phe-Leu-Leu-Val and Leu-Leu-Val-Pro (subsequences of SEQ ID NO:1). As used herein, an available fibrinogen binding domain means a peptide sequence which is sterically available to bind with fibrinogen in the surrounding solution and which adopts a conformation that ligates fibrinogen with moderate to strong avidity under controlled conditions of pH, ionic strength, and solvent composition. The avidity of binding may be increased or decreased by altering the amino acids adjacent to the above listed sequences and/or by terminal deletion of amino acids. The avidity may be modified further by altering the above mentioned conditions of pH, ionic strength, and solvent composition.

The sequences of the more preferred peptides having available fibrinogen binding domains are Phe-Leu-Leu-Val-Pro-Leu, Pro-Leu-Leu-Val-Pro-Leu, and Phe-Ala-Leu-Val-Pro-Leu (SEQ ID NOS 1, 2, and 3, respectively), and the sequence of the most preferred peptide is Phe-Leu-Leu-Val-Pro-Leu (SEQ ID NO:1). The peptides were isolated and identified using a screening process described in U.S. patent application Ser. No. 08/438,331 filed May 10, 1995 in the name of Joseph A. Buettner. We also describe a method of using the peptides in an affinity chromatography process to purify fibrinogen, wherein the method comprises passing a fibrinogen containing solution over a substrate which has bound thereupon peptides disclosed herein, and then eluting the fibrinogen.

The peptides FLLVPL, PLLVPL and FALVPL (SEQ ID NOS 1, 2, and 3, respectively) described herein have been compared to the protein sequence databases and do not show homology to proteins known to interact with the blood clotting components relevant to fibrinogen. Exact matches to FLLVPL (SEQ ID NO:1)are the interleukin-6 receptor (mouse and human), to a hypothetical membrane protein of yeast (*Saccharomyces cervisiae*), a nodule forming protein for *Rhizobium leguminosarum*, and a bovine sodium-dependent phosphate transporter. Exact matches to PLLVPL (SEQ ID NO:2) are the *Chlamydia trachomatis* CMP-2-keto-3-deoxyoctulosonic acid synthetase (kdsB) and CTP synthetase (pyrG) genes, mismatch repair protein mutl protein of *Escherichia coli* and *Salmonella typhimurium*, the human adenovirus 2 late L2 mu core protein precursor, the hypothetical 14K protein (mer operon) of *Staphylococcus aureus* plasmid pI258, a hypothetical protein of *Bacillus subtilis*, a human mitochondria open reading frame (ORF) protein, the POU-c transcription factor of *Brachydanio rerio* (zebra fish), and the H$^+$-transporting ATP synthase. EC 3.6.1.34) chain a of *Synechocystis sp*. Exact matches to FALVPL (SEQ ID NO:3) are the human MLL-AF4 der (11) fusion protein, the human 140 kd serine/proline-rich protein, human protein encoded by the AF-4 mRNA, the protein lmbE of Mycobacterium, and the V0 protein of Miscanthus streak virus.

SPECIFIC EMBODIMENTS

Materials

Polyclonal rabbit antibody to fibrinogen was purchased from American Diagnostical (Greenwich, Conn.) and from Enzyme Research Labs (South Bend, Ind.). The second antibody conjugate, goat anti-rabbit IgG-alkaline phosphatase, and the dye substrates NBT/BCIP and Fast Red TR were from Pierce Chemical Co. (Rockford, Ill.). Human fibrinogen was purchased from Sigma Chemical Co. (St. Louis, Mo.) and from Chromogenix AB (Molndal, Sweden). Fmoc amino acids were from Novobiochem. All other chemicals were reagent grade or better.

General Methods

Screening of the peptide libraries was performed in 2.1 mm×15 cm columns on a microbore HPLC (Microme Bioresources, Auburn, Calif.). Peptides and a 6-mer combinatorial library were synthesized on Toyopearl AF Chelate 650 M (Tosohaas, Montgomeryville, Pa.) modified with 4,7,10-trioxa-1,13-tridecanediamine (Totda; Aldrich, St. Louis, Mo.), using standard Fmoc chemistry as described by Buettner et al. (1996). Peptides were synthesized robotically by using a Gilson AMS 422. Peptide densities achieved with the above scheme were typically in the range of 0.2–0.5 mmole/g resin.

For screening peptides in an affinity chromatographic format, a somewhat lower peptide density would be more desirable to reduce the risk of low capacity of fibrinogen binding due to steric hindrance. Such desirable densitites, as practiced in the usual art of affinity chromatography, would be in the range of 0.05–0.2 mmole/g resin (10 to 40 mg/ml resin). In order to control the density of peptide synthesized onto the Totda linker, mixtures containing varied ratios of Fmoc-L-alanine to t-Boc-L-alanine were coupled to Totda-Toyopearl. Mixtures were made by serial dilution of equal concentrations of stock Fmoc-L-alanine into t-Boc-L-alanine (1:0, 1:5, 1:10, 1:25, and 1:125). The total amino acid concentration was held constant at approximately 2.5 mmole/g resin (five-fold over Totda). After coupling the mixture using standard Fmoc conditions practiced in the art, the Fmoc protecting group was released by alkali, whereas the alkaline resistant t-Boc was not. This residual t-Boc derivatized L-alanine lacked a primary amine and was not available for further peptide synthesis. Peptides were then synthesized onto the resin using Fmoc-derivatized amino acids, followed by deprotection under acid conditions (which also released the residual t-Boc). The density of peptide on batches of resin was determined by total amino acid analysis of dessicated, weighed samples by standard methods. The optimum peptide density was achieved with a mixture of Fmoc to t-Boc of 1:10.

Rink resin (Novobiochem) was used for syntheses when soluble, purified peptides were required as soluble binding ligands. Peptides were cleaved and deprotected and purified by reverse phase HPLC. Alternatively, some peptides required for affinity chromatography were deprotected and cleaved from Rink resin without removal of the N- terminal Fmoc group, purified by reverse phase HPLC and coupled to A-Totda-Toyopearl. Purity of peptides was assessed by analytical reverse phase HPLC and compositions confirmed by FAB mass spectrometry.

Analytical Methods

Sodium dodecylsulfate polyacrylamide gel electrophoresis (SDS-PAGE) was performed in 8% polyacrylamide gels (Novex, San Diego, Calif.) according to the procedure of Laemmli (1970), loading 4 µg protein per lane. Transfer of protein from gels was performed by the method of Towbin et al. (1979) using casein (Pierce Chemical Co.) to block unused membrane binding sites. Bound antibodies were detected by using the chemiluminescent substrate CSPD (Tropix, Bedford, Mass.) and exposure to XAR film (Eastman Kodak, Rochester, N.Y.). Immunonephelometry was performed by using a Behring Nephelometer, model BNA, with assay kits purchased from Behringwerke AG (Marburg, DEU).

Isothermal titration colorimetry was performed using either purified, soluble peptides (5 mM) or peptides synthesized directly on A-Totda-Togopearl (1.4mM) and with purified fibrinogen (50 µM) by a modification of the technique of Tyler-Cross et at. (1993). All measurements were performed at 30° C. in 30 mM phosphate buffer, pH 7.0 with an Omega titration colorimeter (Microcal, Inc., Northampton, Mass.).

Discovery of Binding Peptides To Fibrinogen

An assay similar to the one used in U.S. patent application Ser. No. 08/438,331 (incorporated herein by reference) was used to deduce peptides that bind fibrinogen. The assay is referred to as the peptide library immunostaining chromatographic analysis or PELICAN technique. Briefly, a 6-mer combinatorial peptide library was synthesized directly onto a TosoHaas chromatography resin, Toyopearl 650M Chelate, modified sequentially by amination with Totda, then addition of a base labile linker hydroxymethylbenzoic acid, and finally a glycine residue (G-HMBA-Totda-Toyopearl), at a final substitution density of approximately 0.1 mmole/g resin. The library was synthesized using F-moc chemistry with 18 of the 20 natural amino acids (excepting cysteine and methionine). Amino termini were partially protected with a methylsulfonylethylcarbonyl group.

The first contactings to the resin (0.5 ml) consisted of the equilibration buffer (20 mM HEPES, pH 6.8 and 0.1M NaCl and 0.1% v/v Tween-20), and then the wash buffer (equilibration buffer containing 1M NaCl). This was followed by sequentially contacting the resin with the individual components of the detection system. These components were, namely, anti-human fibrinogen (affinity purified IgG fraction), a second antibody conjugated with alkaline phosphatase, and BCIP/NBT blue stain. All proteins were in equilibration buffer and were followed with wash buffer.

The resin was further contacted with 0.625 µg of fibrinogen (2 nM) in equilibration buffer, followed by the detection system using Fast Red as the stain, as outlined above and in Buettner, et al. (1996).

Blue beads, which indicated non-specific interactions with the detection system, were uniformly found throughout the column at <0.1%; red beads were found uniformly throughout the column at <0.01%. Individual beads were isolated, the peptide cleaved off the bead with 20% triethylamine in methanol with sonication for 2 hours. The cleaved peptide was dried and sequenced by Edman degradation. The amino acid sequence data are given below (Table 1). For cycles where there were ambiguous calls, the amino acids with the highest responses are listed on the first line, and those with lower yields on subsequent lines:

TABLE 1

| Amino acid assignments from N-terminal sequencing of a single red bead. |
| --- |
| Sequence |
| Phe Leu Leu Val Pro Leu |
| Pro Ala |
| Ala |

Figure 1:
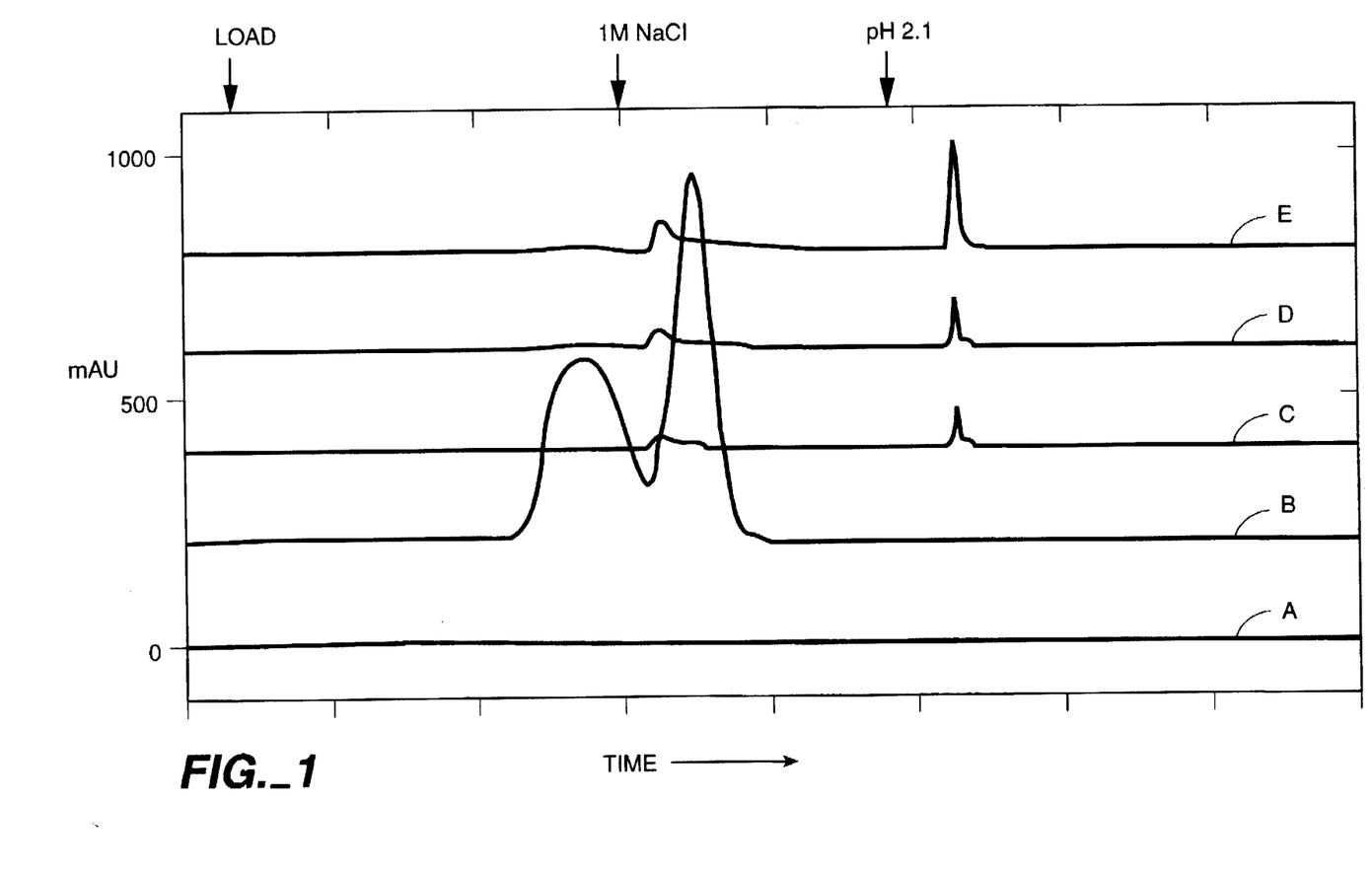
FIG. 1 shows elution profiles (absorbance at 280 nm) of chromatographic separations on peptide PLLVPL-A-Totda-Toyopearl. (SEQ ID NO 2) A) buffers, no protein; B) 0.5 mg hSA; C) 250 µg fibrinogen; D) 500 µg fibrinogen; E) 1000 µg fibrinogen. Fibrinogen was applied at approximately 17 µl/min for 10 min, and then the column was washed with equilibration buffer for 4 min at 865 µl/min, followed by equilibration buffer containing 1.0M NaCl for 5 min, 3.0M NaCl for a further 5 min, and 0.1M for another 5 min. Protein was eluted between 30 to 35 min by using 2% acetic acid.
Figure 2:
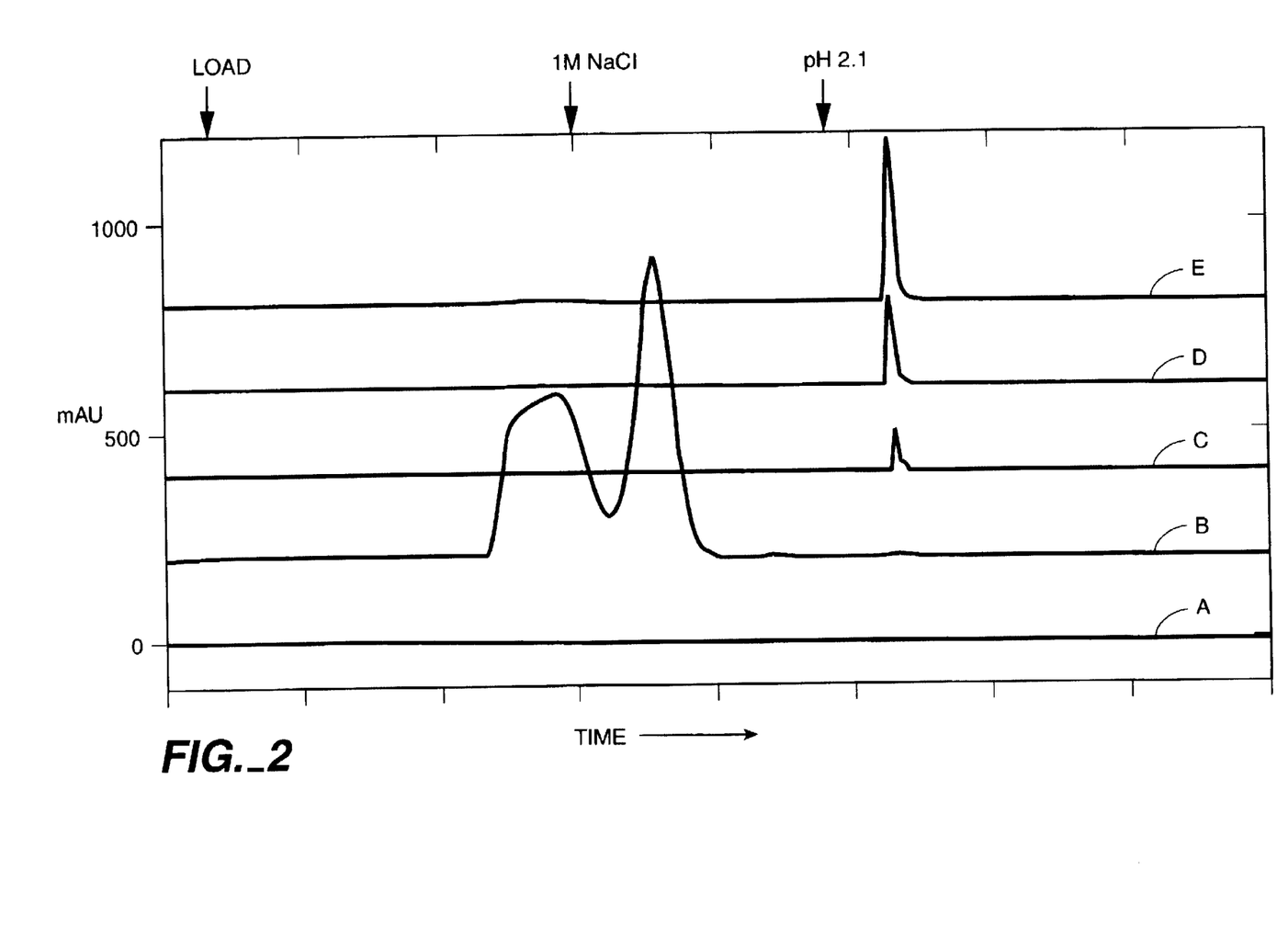
FIG. 2 shows elution profiles (absorbance at 280 nm) of chromatographic separations on peptide FLLVPL-A-Totda-Toyopearl. (SEQ ID NO 1) Line designations are the same as in FIG. 1. Elution conditions are the same as in FIG. 1.

Confirmatory binding assays were performed in a column chromatographic format on a microbore HPLC using individual peptide sequences synthesized directly onto the Toyopearl 650M Chelate resin which had been modified with Totda followed by an alanine residue (A-Totda-Toyopearl), at a final substitution density of 0.2 mmole/g resin. Contactings to resins (FIG. 1 and 2, for PLLVPL and FLLVPL resins, respectively (SEQ ID NOS 2 and 1, respectively)) included A) equilibration buffer (as above), wash buffer (as above), and elution buffer (2.5% acetic acid) only; B) human serum albumin in equilibration buffer (hSA; 0.5 mg), followed by wash and elution buffers, C-E) graded dosages (250, 500, and 1000 µg) of purified fibrinogen in equilibration buffer, followed by wash and elution buffers. The endpoint was a dose-dependent increase in the acid eluate in the fibrinogen contactings, and quantification was by integration of the absorbance at 280 nm (Table 2).

TABLE 2

| Binding analysis of peptides synthesized on A-Totda-Toyopearl. | | | | |
| --- | --- | --- | --- | --- |
| | | 2% Acetic Acid Eluate, A280 (µg Fibrinogen Applied) | | |
| SEQ ID NO | Sequence | 250 | 500 | 1000 |
| 1 | FLLVPL | 1.54 | 3.23 | 6.92 |
| 2 | PLLVPL | 0.99 | 1.70 | 4.41 |
| 3 | FALVPL | 0.72 | 1.35 | 2.78 |
| 6 | PALVPL | 0.01 | 0.06 | 0.13 |
| 7 | ALLVPL | 0.02 | 0.09 | 0.12 |
| 8 | AALVPL | 0.02 | 0.09 | 0.12 |

Figure 3A:
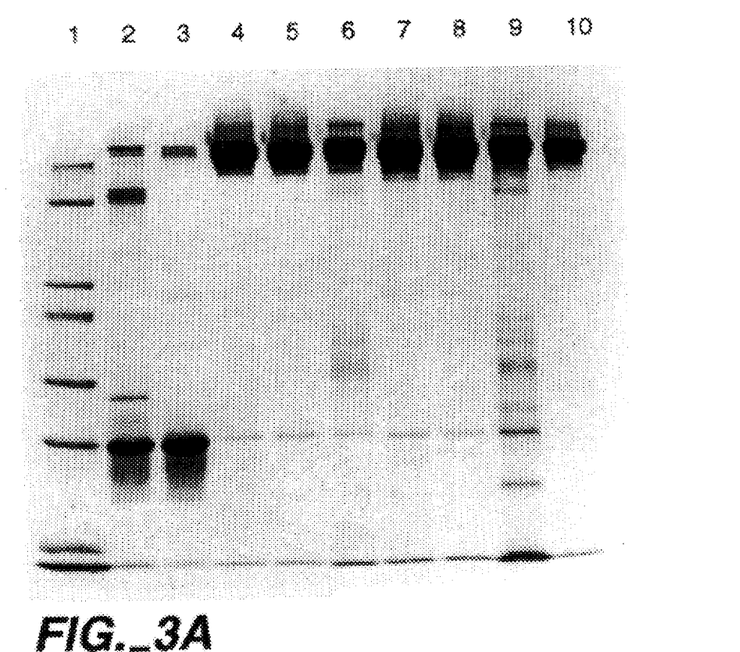
FIG. 3A shows a Coomassie-stained SDS-PAGE of plasma, fibrinogen and hSA mixture and acid eluates from chromatographic separations. Lane 1, molecular weight standards; lane 2, human plasma; lane 3, fibrinogen/hSA mixture; lane 4, acid eluate from fibrinogen/hSA mixture (no Tween) applied to PLLVPL-resin (SEQ ID NO 2); lane 5, acid eluate, same as lane 4 (with Tween); lane 6, acid eluate of human plasma; lane 7–9, same as lanes 4–6 using FLLVPL-resin (SEQ ID NO 1); lane 10, fibrinogen standard.
Figure 3B:
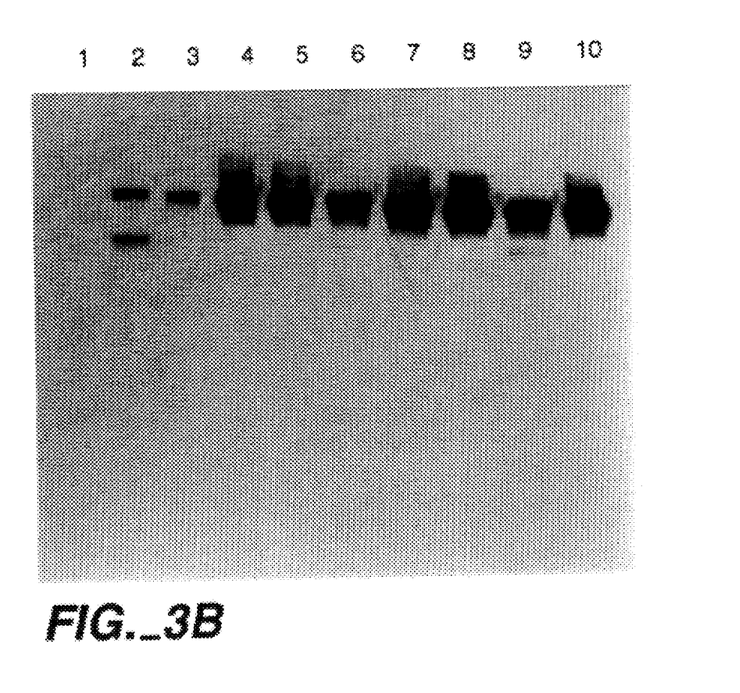
FIG. 3B shows a Western blot analysis of a duplicate gel to the one shown in FIG. 3A.

There was a dose dependent increase in binding of fibrinogen to resins FLLVPL-A-Totda-Toyopearl, PLLVPL-A-Totda-Toyopearl, and to a lesser extent, to FALVPL-A-Totda-Toyopearl (SEQ ID NOS 1, 2, and 3, respectively). These resins were contacted with a mixture of fibrinogen (100 µg) and hSA (0.5 mg) in equilibration buffer in the presence or absence of 0.1% (v/v) Tween-20, a nonionic detergent used to lower non-specific binding and also used as a viral inactivating agent. The resins were washed with wash buffer (without Tween-20) and 2% acetic acid. Analysis of the acid eluates by SDS-PAGE (FIG. 3A, lanes 4–5 and 7–8) revealed that the vast majority of the protein that bound PLLVPL and FLLVPL (SEQ ID NOS 2 and 1, respectively) resins was of a molecular weight equivalent to fibrinogen (340,000) that co-migrated with purified fibrinogen standard (lane 10). This protein was greatly enriched from the starting mixture (FIG. 3A, lane 3). Western blotting with an antibody to human fibrinogen confirmed the identity of this protein as fibrinogen (FIG. 3B). The presence of Tween-20 in the buffer system did not affect binding of fibrinogen to either peptide as indicated by the amounts of protein recovered in the acid eluate. Tween was therefore removed from the fibrinogen solution by washing the column.

TABLE 3

Thermodynamics of binding between fibrinogen and either soluble or resin bound peptides identified by the PELICAN technique. Measurements by isothermal titration calorimetry at 30° C.; the titration curves were normal isotherms. PLLVPL is SEQ ID NO 2; FLLVPL is SEQ ID NO 1. nd = not determined; na = not applicable

| Sequence | $K_D$ (µM) | ΔH (kcal/mol) | ΔS (eu) | N | ΔG (kcal/mol) |
| --- | --- | --- | --- | --- | --- |
| Solution phase binding | | | | | |
| PLLVPL | 688 | +1.22 | +18.9 | 3.45 | −4.38 |
| FLLVPL | 4.5 | +10.9 | +64.5 | 0.97 | −7.41 |
| Resin binding | | | | | |
| PLLVPL-A-Totda-Toyopearl | nd | nd | nd | nd | nd |
| FLLVPL-A-Totda-Toyopearl | 0.03 | +228 | +870 | na | −10.46 |

Solution phase binding isotherms were performed on the purified soluble peptides and purified fibrinogen by using isothermal titration calorimetry (Table 3). The sequence PLLVPL (SEQ ID NO:2) showed weaker solution binding to fibrinogen than FLLVPL (SEQ ID NO:1) under the conditions used. A change from P to F at the amino terminus lowered the dissociation constant over 150-fold. PLLVPL (SEQ ID NO:2) bound to approximately 3 to 4 sites per fibrinogen molecule. These interactions had a large, positive entropic term which may indicate that a conformational change occurred in either the peptide or in fibrinogen. The sequence FLLVPL (SEQ ID NO:1) bound at approximately one site on fibrinogen, and this binding also had a very large, positive entropy. Both peptide binding reactions were endothermic as indicated by the positive enthalpy (ΔH), and were thermodynamically favorable (negative ΔG) under the conditions tested. Unusually high entropic terms indicate a conformational change may be driving the association of peptide with fibrinogen.

The apparent dissociation constant of FLLVPL (SEQ ID NO:1) synthesized on A-Totda-Toyopearl decreased over 100-fold from that of the soluble peptide. The increased magnitude of the enthalpic and entropic terms suggest a similar mechanism of binding to fibrinogen as compared to soluble peptide. The free energy of binding remained favorable.

EXAMPLE 1

Purification Of Fibrinogen From Plasma By Using FLLVPL and PLLVPL Resins (SEQ ID NOS 1 and 2, respectively)

Figure 4:
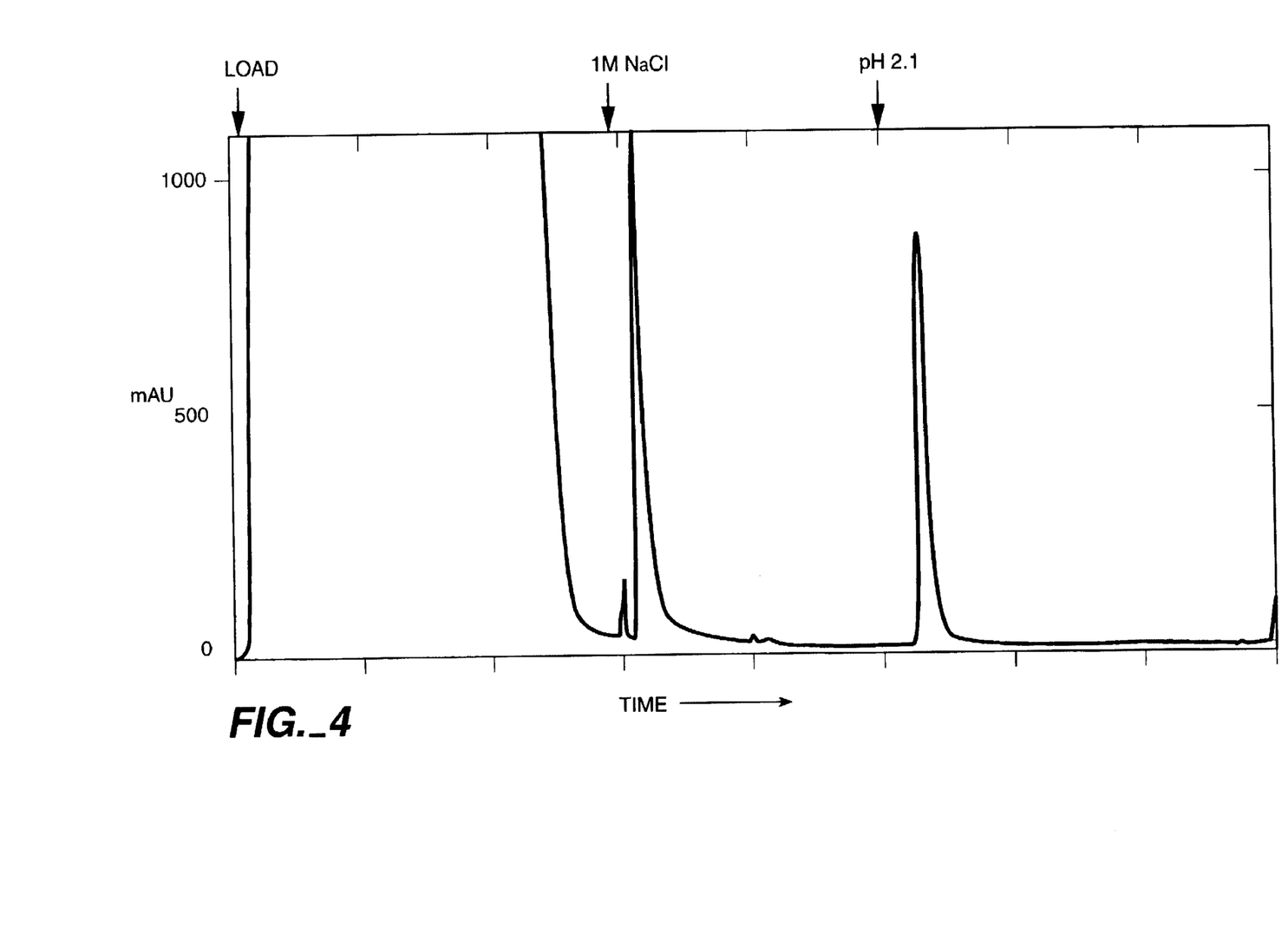
FIG. 4 shows the elution profile (absorbance at 280 nm) of whole plasma applied to PLLVPL-A-Totda-Toyopearl (SEQ ID NO 2). Elution conditions are the same as in FIG. 1.
Figure 5:
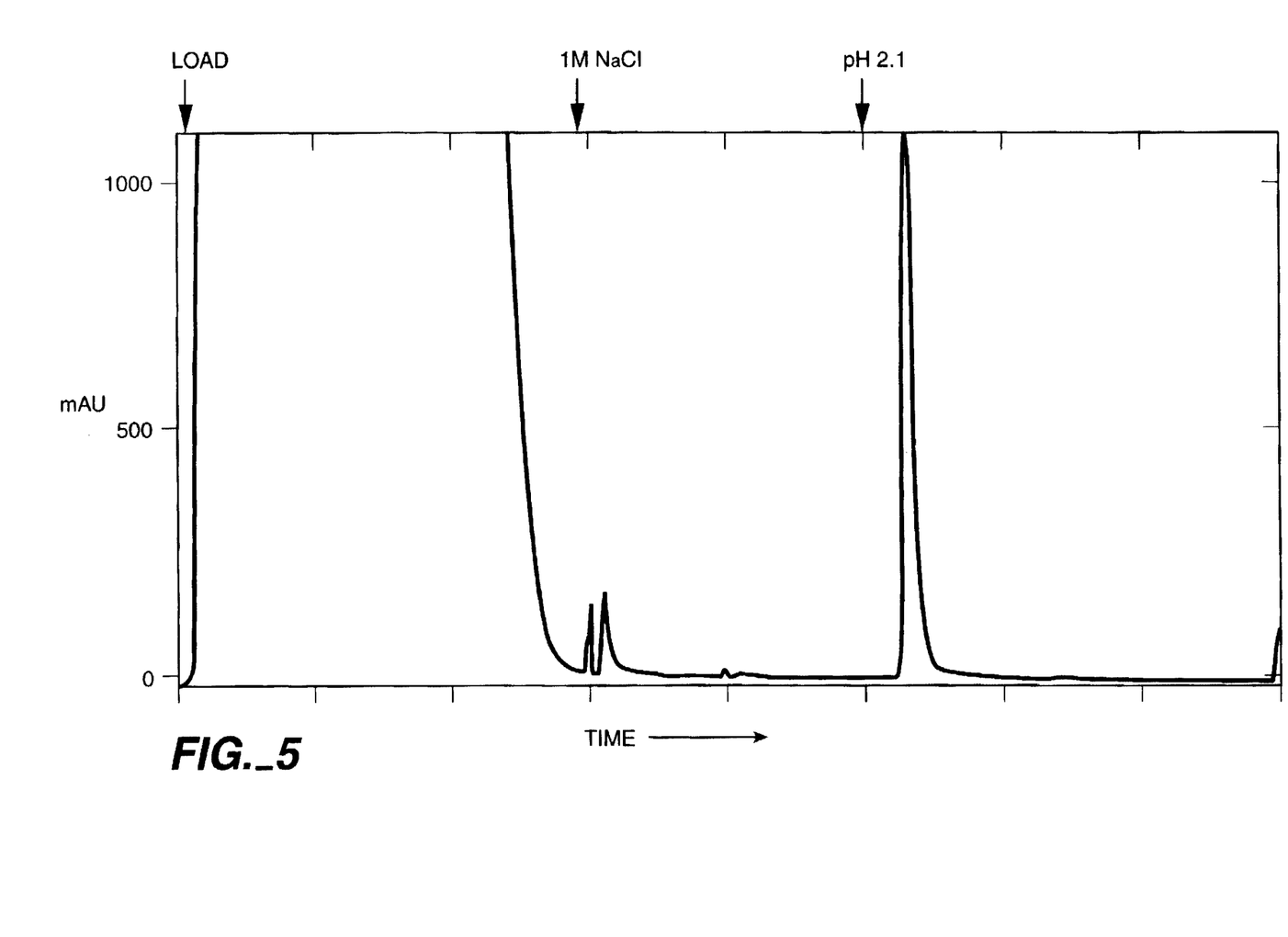
FIG. 5 shows the elution profile (absorbance at 280 nm) of whole plasma applied to FLLVPL-A-Totda-Toyopearl (SEQ ID NO 1). Elution conditions are the same as in FIG. 1.

Human plasma was diluted 1:2 in equilibration buffer containing 0.1% (v/v) Tween-20. Wash and elution conditions were as outlined above. Approximately 1.0 ml was injected onto the peptide resin PLLVPL-A-Totda-Toyopearl and FLLVPL-A-Totda-Toyopearl (SEQ ID NOS 2 and 1, respectively) (FIGS. 4 and 5, respectively). Acid treatment was used to release protein from the peptide resins. Whole plasma, freshly frozen and thawed and with cryoprecipitate removed by centrifugation, was analyzed by SDS-PAGE (FIG. 3A, lane 2). Plasma contained fibrinogen bands near the top of the gel whose identity was confirmed by western blotting (FIG. 3B, lane 2). Acid eluates contained highly purified fibrinogen (FIG. 3A and B, lanes 6 and 9).

The acid eluate fraction from the FLLVPL (SEQ ID NO:1) resin separations was analyzed by immunonephelometry for fibrinogen and several other plasma proteins after adjusting the pH to neutrality with 1M TrisHCl, pH 8.0 (Table 4).

TABLE 4

Quantification of plasma proteins in diluted plasma and in acid eluate from FLLVPL-A-Totda-Toyopearl (SEQ ID NO 1).

|  | Initial Plasma mg | Acid Eluate mg (%) |
|---|---|---|
| Fibrinogen | 1.53 | 0.90 (58.8) |
| Fibronectin | 0.20 | <0.02 |
| IgG | 3.28 | <0.01 |
| IgM | 0.27 | 0.02 (7.5) |
| Antithrombin-III | 0.17 | <0.03 |
| Transferrin | 1.02 | <0.08 |
| hSA | 22.9 | <0.35 |
| $\alpha_2$-Macroglobulin | 0.98 | <0.05 |
| Haptoglobin | 0.63 | <0.07 |
| Ceruloplasmin | 0.14 | <0.02 |

No other serum protein was detected in the acid eluate other than fibrinogen and a small amount of IgM by using this assay. The low recovery of immunoreactive fibrinogen (58.8%) reflects the loss of antigenicity due to low pH exposure. All other tested plasma proteins were below detection limits.

EXAMPLE 2

Further Characterization of Binding Sequence

Peptides PLLVPL and FLLVPL, with and without an N-acetylated amino terminus, were synthesized directly onto Ala-Totda-Toyopearl at a density of approximately 0.2 mmole/g resin. The ability of these resins to bind fibrinogen was determined as above. An unblocked (free) amino terminus was required for binding fibrinogen to PLLVPL-A-Totda-Toyopearl (Table 5) (SEQ ID NO:2). Similar results were obtained in a separate experiment by using FLLVPL-A-Totda-Toyopearl (Table 5) (SEQ ID NO:1).

TABLE 5

N-acetylated vs. free amino terminus. PLLVPL is SEQ ID NO 2; FLLVPL is SEQ ID NO 1

| Sequence | 2% Acetic Acid Eluate, A280 (µg Fibrinogen Applied) | | |
|---|---|---|---|
|  | 250 | 500 | 1000 |
| PLLVPL | 0.60 | 1.18 | 2.40 |
| N-acetyl-PLLVPL | 0.02 | 0.05 | 0.07 |

TABLE 5-continued

N-acetylated vs. free amino terminus. PLLVPL is SEQ ID NO 2; FLLVPL is SEQ ID NO 1

| Sequence | 2% Acetic Acid Eluate, A280 (µg Fibrinogen Applied) | | |
|---|---|---|---|
|  | 250 | 500 | 1000 |
| FLLVPL | 1.57 | 2.99 | 4.36 |
| N-acetyl-FLLVPL | 0.00 | 0.00 | 0.13 |

Truncations from the carboxyl- and amino- termini of PLLVPL and FLLVPL (SEQ ID NOS 2 and 1, respectively) synthesized directly on A-Totda-Toyopearl resin in order to identify the minimum sequence necessary for binding. Table 6 shows the qualification of eluates from the resins contacted in chromatographic format with graded dosages of fibrinogen.

TABLE 6

| Peptide Sequence | Fraction (Absorbance 280 nm) | | | | | |
|---|---|---|---|---|---|---|
|  | 1 M NaCl Eluate, (µg Fibrinogen Applied) | | | 2% Acetic Acid Eluate, (µg Fibrinogen Applied) | | |
|  | 250 | 500 | 1000 | 250 | 500 | 1000 |
| P | 0.32 | 0.70 | 1.59 | 0.00 | 0.01 | 0.02 |
| PL | 0.84 | 1.68 | 3.33 | 0.00 | 0.02 | 0.04 |
| PLL | 1.31 | 2.85 | 5.76 | 0.00 | 0.02 | 0.05 |
| PLLV | 1.27 | 2.79 | 5.81 | 0.00 | 0.00 | 0.04 |
| PLLVP | 1.29 | 3.01 | 5.99 | 0.00 | 0.03 | 0.09 |
| PLLVPL | 0.17 | 0.54 | 1.58 | 0.71 | 1.44 | 3.10 |
| PLLVPL | 0.10 | 0.33 | 1.05 | 1.07 | 2.15 | 4.87 |
| LLVPL | 0.96 | 2.13 | 5.11 | 0.14 | 0.30 | 0.59 |
| LVPL | 0.88 | 2.02 | 3.67 | 0.00 | 0.02 | 0.07 |
| VPL | 0.68 | 1.37 | 2.84 | 0.00 | 0.02 | 0.03 |
| PL | 0.75 | 1.50 | 3.07 | 0.00 | 0.01 | 0.03 |
| L | 0.38 | 0.79 | 1.76 | 0.00 | 0.01 | 0.03 |
| FL | 0.00 | 0.23 | 2.48 | 0.00 | 0.00 | 0.19 |
| FLL | 0.00 | 0.16 | 0.77 | 0.90 | 1.01 | 2.67 |
| FLLV | 0.00 | 0.00 | 0.50 | 1.51 | 1.79 | 4.99 |
| FLLVP | 0.00 | 0.00 | 0.16 | 0.75 | 1.41 | 3.75 |
| FLLVPL | 0.00 | 0.00 | 0.17 | 1.04 | 2.03 | 4.47 |
| FLLVPL | 0.00 | 0.00 | 0.00 | 1.57 | 2.99 | 4.36 |
| LLVPL | 0.00 | 0.43 | 0.82 | 0.59 | 1.08 | 2.25 |
| LVPL | 0.30 | 1.06 | 2.55 | 0.00 | 0.00 | 0.15 |
| VPL | 0.00 | 0.00 | 0.11 | 0.00 | 0.00 | 0.38 |
| PL | 0.00 | 0.00 | 0.00 | 0.00 | 0.00 | 0.30 |

Three different amounts of fibrinogen were injected onto the indicated peptide columns (250 µg, 500 µg and 1 mg). Numbers indicate the integration of the absorbance at 280 nm ($\times 10^6$) for the 1 M NaCl wash peak and the acid elution peak for each amount of fibrinogen injected. The amount of fibrinogen in the flow through is not included. PLLVPL and truncations are SEQ ID NO 2; FLLVPL and truncations are SEQ ID NO 1.

The full length peptides (e.g., 6-mers) bound fibrinogen most tightly for all three injection amounts (250, 500 and 1000 µg) as reflected in the amount released at low pH, although there was a smaller but proportional increase in the amount released by 1M NaCl. Truncations from the C-terminus yielded peptides which bound fibrinogen less tightly, as indicated by a greater amount released by 1M NaCl. Similar results were observed for the N-terminal truncation peptides. These results indicate that the entire peptide sequence of six amino acids is necessary for optimal binding to fibrinogen under the conditions tested. Additionally, modifications to the length of the peptide may allow for more gentle elution conditions than with low pH. Peptides which are four amino acids long (4-mers) bind well, with peptides which are five amino acids long (5-mers)

being more preferred, and peptides which are six amino acids long (6-mers) being most preferred. It is anticipated that peptides which are seven (7-mers) or more amino acids long which contain the sequences disclosed herein would also be suitable for binding fibrinogen if the binding domains are accessible, or available, to be bound by the fibrinogen, as defined above.

EXAMPLE 3

Further Characterization of Binding Interaction

Peptide FLLVPL was synthesized directly on A-Totda-Toyopearl at a density of 0.2 mmole/g resin. A column of dimensions 1.0×6.4 cm (approximately 5 ml column volume) was equilibrated with either 10 mM HEPES or 10 mM sodium acetate, pH 6.8, 1.0 mM EGTA and either 0.1, 0.2 or 1.0M NaCl. Fibrinogen (25 mg; 5.0 ml) was applied to the column in 10 mM sodium acetate, pH 6.8 and 1 mM EGTA containing 0.1M NaCl. Under these conditions, approximately 5 to 8 % of the applied absorbance (280 nm) failed to bind the column. Thus binding was unaffected by increased ionic strength, suggesting a significant role for hydrophobic binding in the peptide-protein interaction.

Fibrinogen (25 mg; 5.0 ml) was applied to the column in 10 mM sodium acetate, pH 6.8 and 1 mM EGTA containing 0.1M NaCl. Elution with a nonionic detergent (5% Tween-20) in the binding buffer resulted in the release of 40 percent of the applied protein, suggesting a role for hydrophobic interactions in the binding. Conversely, elution with an ionic (2% sodium cholate) detergent resulted in only 14 percent release.

No elution of fibrinogen (applied to the column in 10 mM sodium acetate, pH 6.8 and 1 mM EGTA containing 0.1M NaCl) was observed by using the hydrophilic compound, polyethylene glycol (10%). Only approximately 8 percent of the applied fibrinogen was eluted by increasing the pH to 10 with 10 mM sodium borate. Further increases in pH with a linear gradient (pH 6.8 to 12.0) released approximately 25 percent of the fibrinogen. On the other hand, use of a pH gradient from 6.8 to 4.0 resulted in approximately 66 percent release of fibrinogen at pH 4.2.

Figure 6:
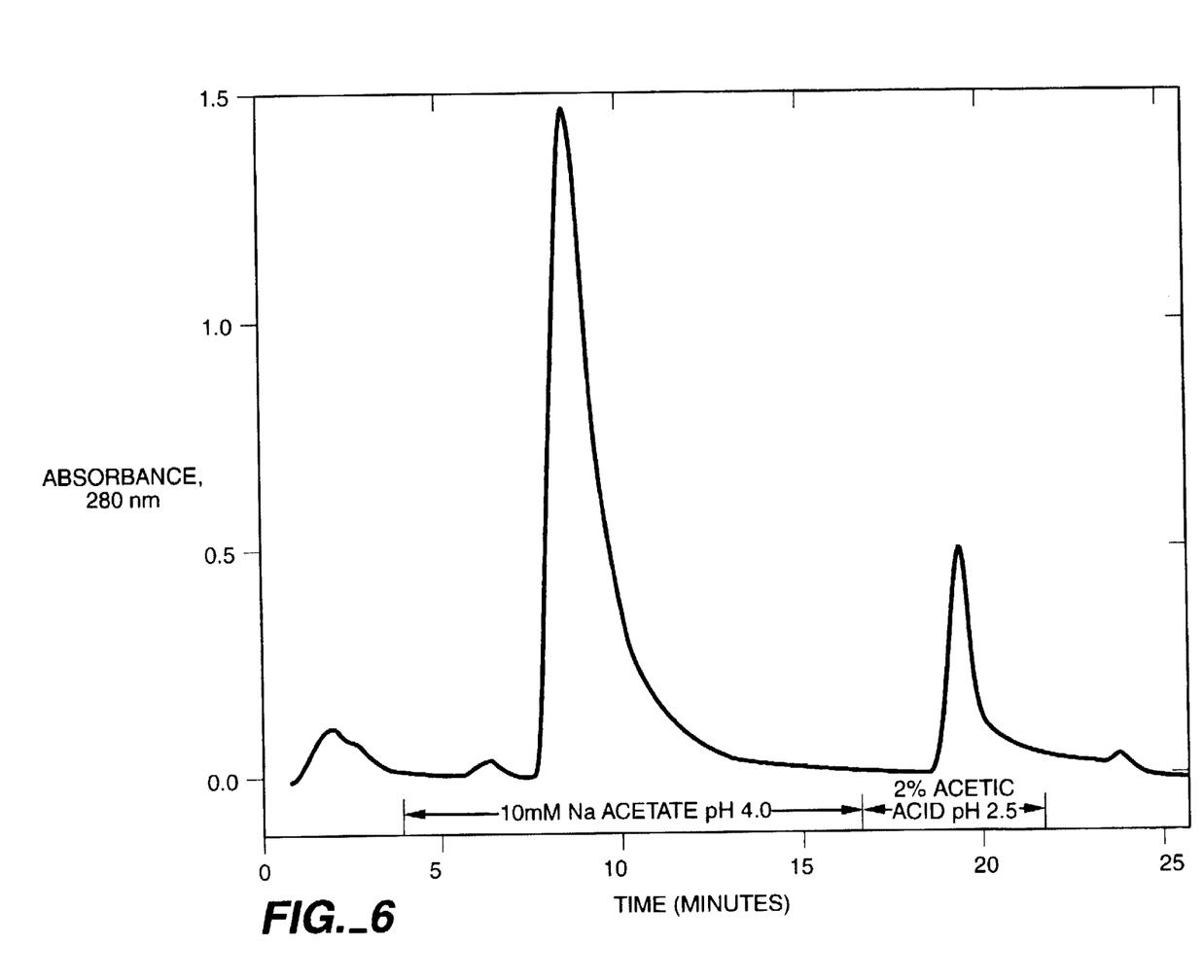
FIG. 6 shows the elution profile of fibrinogen applied to FLLVPL-A-Totda-Toyopearl (SEQ ID NO 1) under conditions of high salt (1M NaCl) at neutral pH (6.8) and elution by low ionic strength (10 mM sodium acetate) at low pH (4.0).

In order to assess further the contribution of hydrophobic interactions to the binding mechanism of FLLVPL (SEQ ID NO.:1) to fibrinogen, fibrinogen (25 mg; 5.0 ml) was applied to the peptide under high salt conditions favorable to hydrophobic bonding and release under low ionic strength. The peptide resin was equilibrated with 10 mM sodium acetate, 1.0M NaCl, and 1.0 mM EGTA, pH 6.8. Five milliliters of a solution of fibrinogen (5 mg/ml) in the same buffer was applied to the column, and washed with two column volumes of the same buffer. The resin was then contacted with 10 column volumes of 10 mM sodium acetate, pH 4.0 followed by 2% acetic acid (4 column volumes). The elution profile is shown in FIG. 6. Approximately 7.2 percent of the applied protein (by absorbance at 280 nm) did not interact with the column and was recovered in the flow through and wash fractions. Low ionic strength and low pH (4.0) released approximately 78.3 percent of the protein. However, only 5% of the applied protein was eluted in a second experiment when the 10 mM sodium acetate, pH 4.0 solution contained 0.1M NaCl. Acid treatment released the remainder of the recovered protein in both experiments. Treatment of the pH 4.0 eluate with α-thrombin after neutralization to pH 6.9 with a stock solution of 0.4M sodium phosphate, pH 11 resulted in the formation of a visible clot. Approximately 88.9% of the total recovered protein in the neutralized acid eluate was clottable with α-thrombin.

These results document that the interaction of fibrinogen with FLLVPL (SEQ ID NO:1 ) is driven by hydrophobic attractions in addition to an ionic interaction with the primary amine at the N-terminus of the protein. Furthermore, these results demonstrated a binding and elution strategy for fibrinogen useful in affinity chromatography.

CONCLUSION

We have demonstrated the use of novel peptides for the affinity purification of fibrinogen. These novel peptides have available fibrinogen binding domains and were obtained by screening peptide libraries and can be readily made in purified form. It is further anticipated that modification of these peptides by conservative substitution, deletion of terminal residues, and/or addition of terminal moieties is a useful technique for altering the selectivity of binding.

The above examples are intended to illustrate the invention and it is thought variations will occur to those skilled in the art. Accordingly, it is intended that the scope of the invention should be limited only by the claims below.

REFERENCES

Blomback, B., & M. Blomback, Ark. Kemi 10:415–443 (1956)
Buettner, J. A. et. al., Int. J. Prot. Peptide Res. (1996) (in press)
Dempfle, C. E., & D. L. Heene, Thromb. Res. 46:19–27 (1987a)
Dempfle, C. E., & D. L. Heene, Thromb. Res. 48:223–232 (1987b)
Furlan, M., Curr. Probl. Clin. Biochem. 14:133–145 (1984)
Jakobsen, E., & P. A. Kierulf, Thromb. Res. 3:145–159 (1973)
Kingdon, H. S. et al., U.S. Pat. No. 5,354,682 (1994)
Kopf, H. B., & B. S. Morse, U.S. Pat. No. 5,259,971 (1993)
Kuyas, C. A. et al., Thromb. Haemost. 63:439–444 (1990)
Laemmli, U. K., Nature 227:680–685 (1970)
Matthias, F. R. et al., Thromb. Res. 7:861–870 (1975)
McConnell, J. P., & D. J. Anderson, J. Chromatog. 615:67–75 (1993)
Merskey, C. et al., Br. J. Haematol. 44:655–670 (1980)
Scholz, W. et al., U.S. Pat. No. 5,210,075 (1993)
Suzuki, K. et al., Thromb. Res. 18:707–715 (1980)
Takeda, Y., J. Clin. Invest. 45:103–111 (1966)
Towbin, H., et al., Proc. Natl. Acad. Sci. (U.S.A.) 76:4350–4354 (1979)
Tyler-Cross, R. et al., Arch. Biohem. Biophys 306:528–533 (1993)

What is claimed is:

1. A composition comprising a peptide 4-mer, 5-mer, or 6-mer having an available fibrinogen binding domain, wherein the binding domain is selected from the group consisting of Phe-Leu-Leu-Val and Leu-Leu-Val-Pro (subsequences of SEQ ID NO:1).

2. The composition of claim 1, wherein the peptide is a 5-mer.

3. The composition of claim 2, wherein the peptide is selected from the group consisting of Phe-Leu-Leu-Val-Pro and Leu-Leu-Val-Pro-Leu (subsequences of SEQ ID NO:1 ).

4. The composition of claim 1, wherein the peptide is a 6-mer.

5. The composition of claim 4, wherein the peptide is selected from the group consisting of Phe-Leu-Leu-Val-Pro-Leu and Pro-Leu-Leu-Val-Pro-Leu (SEQ ID NOS 1 and 2, respectively).

6. A composition comprising a peptide having an available fibrinogen binding domain, wherein the binding domain is selected from the group consisting of Phe-Leu-Leu-Val-Pro-Leu, Pro-Leu-Leu-Val-Pro-Leu, and Phe-Ala-Leu-Val-Pro-Leu (SEQ ID NOS 1, 2, and 3, respectively).

7. A method of purifying fibrinogen comprising contacting a solution containing fibrinogen with a substrate under conditions sufficient to bind fibrinogen to the substrate, wherein the substrate comprises peptides bound to a support material, wherein the peptides have an available fibrinogen binding domain selected from the group consisting of Phe-Leu-Leu-Val and Leu-Leu-Val-Pro (subsequences of SEQ ID NO:1).

8. A method of purifying fibrinogen comprising contacting a solution containing fibrinogen with a substrate under conditions sufficient to bind fibrinogen to the substrate, wherein the substrate comprises peptides bound to a support material, wherein the peptides have an available fibrinogen binding domain selected from the group consisting of Phe-Leu-Leu-Val-Pro-Leu, Pro-Leu-Leu-Val-Pro-Leu, and Phe-Ala-Leu-Val-Pro-Leu (SEQ ID NOS 1, 2, and 3, respectively).

9. Peptides selected from the group consisting of Phe-Leu-Leu-Val-Pro-Leu, Pro-Leu-Leu-Val-Pro-Leu, and Phe-Ala-Leu-Val-Pro-Leu (SEQ ID NOS 1, 2, and 3, respectively).

10. Peptides selected from the group consisting of Phe-Leu-Leu-Val-Pro, Phe-Leu-Leu-Val, and Leu-Leu-Val-Pro-Leu (subsequences of SEQ ID NO:1).

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 6
      ( B ) TYPE: amino acid
      ( C ) STRANDEDNESS: single strand
      ( D ) TOPOLOGY: linear ( i i ) MOLECULE TYPE:
      ( A ) DESCRIPTION: peptide ( x i ) SEQUENCE DESCRIPTION: SEQ ID NO:1:

Phe Leu Leu Val Pro Leu
 1               5

( 2 ) INFORMATION FOR SEQ ID NO:2:

( i ) SEQUENCE CHARACTERISTICS:
      ( A ) LENGTH: 6
      ( B ) TYPE: amino acid
      ( C ) STRANDEDNESS: single strand
      ( D ) TOPOLOGY: linear ( i i ) MOLECULE TYPE:
      ( A ) DESCRIPTION: peptide ( x i ) SEQUENCE DESCRIPTION: SEQ ID NO:2:

Pro Leu Leu Val Pro Leu
 1               5

( 2 ) INFORMATION FOR SEQ ID NO:3:

( i ) SEQUENCE CHARACTERISTICS:
      ( A ) LENGTH: 6
      ( B ) TYPE: amino acid
      ( C ) STRANDEDNESS: single strand
      ( D ) TOPOLOGY: linear ( i i ) MOLECULE TYPE:
      ( A ) DESCRIPTION: peptide ( x i ) SEQUENCE DESCRIPTION: SEQ ID NO:3:

Phe Ala Leu Val Pro Leu
 1               5

( 2 ) INFORMATION FOR SEQ ID NO:4:

( i ) SEQUENCE CHARACTERISTICS:
      ( A ) LENGTH: 5
      ( B ) TYPE: amino acid
      ( C ) STRANDEDNESS: single strand
      ( D ) TOPOLOGY: linear ( i i ) MOLECULE TYPE:
      ( A ) DESCRIPTION: peptide ( x ) PUBLICATION INFORMATION:
      ( A ) AUTHORS: Kuyas, C.
             Haeberli, A.
             Walder, P.
             Straub, P. W.
      ( B ) TITLE: Isolation of Human Fibrinogen and its
             Derivatives by Affinity Chromatography on Gly-Pro-
             Arg-Pro-Lys- Fractogel
      ( C ) JOURNAL: Thromb. Haemost.
      ( D ) VOLUME: 63

( E ) ISSUE: 3
                    ( F ) PAGES: 439-444
                    ( G ) DATE: 28-JUN-1990

( x i ) SEQUENCE DESCRIPTION: SEQ ID NO:4:

Gly Pro Arg Pro Lys
1                 5

( 2 ) INFORMATION FOR SEQ ID NO:5:

( i ) SEQUENCE CHARACTERISTICS:
                ( A ) LENGTH: 9
                ( B ) TYPE: amino acid
                ( C ) STRANDEDNESS: single strand
                ( D ) TOPOLOGY: linear ( i i ) MOLECULE TYPE:
                ( A ) DESCRIPTION: peptide ( x ) PUBLICATION INFORMATION:
                ( A ) AUTHORS: Kuyas, C.
                               Haeberli, A.
                               Walder, P.
                               Straub, P. W.
                ( B ) TITLE: Isolation of Human Fibrinogen and its
                             Derivatives by Affinity Chromatography on Gly-Pro-
                             Arg-Pro-Lys- Fractogel
                ( C ) JOURNAL: Thromb. Haemost.
                ( D ) VOLUME: 63
                ( E ) ISSUE: 3
                ( F ) PAGES: 439-444
                ( G ) DATE: 28-JUN-1990

( x i ) SEQUENCE DESCRIPTION: SEQ ID NO:5:

Gly Pro Arg Val Val Glu Arg His Lys
1                 5

( 2 ) INFORMATION FOR SEQ ID NO:6:

( i ) SEQUENCE CHARACTERISTICS:
                ( A ) LENGTH: 6
                ( B ) TYPE: amino acid
                ( C ) STRANDEDNESS: single strand
                ( D ) TOPOLOGY: linear ( i i ) MOLECULE TYPE:
                ( A ) DESCRIPTION: peptide ( x i ) SEQUENCE DESCRIPTION: SEQ ID NO:6:

Pro Ala Leu Val Pro Leu
1                 5

( 2 ) INFORMATION FOR SEQ ID NO:7:

( i ) SEQUENCE CHARACTERISTICS:
                ( A ) LENGTH: 6
                ( B ) TYPE: amino acid
                ( C ) STRANDEDNESS: single strand
                ( D ) TOPOLOGY: linear ( i i ) MOLECULE TYPE:
                ( A ) DESCRIPTION: peptide ( x i ) SEQUENCE DESCRIPTION: SEQ ID NO:7:

Ala Leu Leu Val Pro Leu
1                 5

( 2 ) INFORMATION FOR SEQ ID NO:8:

( i ) SEQUENCE CHARACTERISTICS:
                ( A ) LENGTH: 6
                ( B ) TYPE: amino acid ( C ) STRANDEDNESS: single strand
( D ) TOPOLOGY: linear ( i i ) MOLECULE TYPE:
( A ) DESCRIPTION: peptide ( x i ) SEQUENCE DESCRIPTION: SEQ ID NO:8:

Ala Ala Leu Val Pro Leu
1                 5